(12) United States Patent
Becker (10) Patent No.: US 11,771,584 B2
(45) Date of Patent: Oct. 3, 2023

(54) URINE COLLECTING BAG

(71) Applicant: Coloplast A/S, Humlebaek (DK)

(72) Inventor: Kim Becker, Hilleroed (DK)

(73) Assignee: Coloplast A/S, Humlebaek (DK)

( * ) Notice: Subject to any disclaimer, the term of this patent is extended or adjusted under 35 U.S.C. 154(b) by 148 days.

(21) Appl. No.: 17/414,957

(22) PCT Filed: Dec. 20, 2019

(86) PCT No.: PCT/DK2019/050418
§ 371 (c)(1),
(2) Date: Jun. 17, 2021

(87) PCT Pub. No.: WO2020/125908
PCT Pub. Date: Jun. 25, 2020

(65) Prior Publication Data
US 2022/0054295 A1    Feb. 24, 2022

(51) Int. Cl.
*A61F 5/44* (2006.01)
*A61F 5/451* (2006.01)
*A61M 25/00* (2006.01)

(52) U.S. Cl.
CPC ............ *A61F 5/4404* (2013.01); *A61F 5/451* (2013.01); *A61M 25/002* (2013.01); *A61M 2202/0496* (2013.01)

(58) Field of Classification Search
CPC .......... A61F 5/4404; A61F 5/451; A61F 5/44; A61M 25/002; A61M 2202/0496
See application file for complete search history.

(56) References Cited

U.S. PATENT DOCUMENTS

| 761,235 | A | 5/1904 | Kepler |
| 1,060,665 | A | 5/1913 | Harlow |
| 1,120,549 | A | 12/1914 | Schellberg |
| 2,856,932 | A | 10/1958 | Griffitts |
| 3,154,080 | A | 10/1964 | Rowan et al. |

(Continued)

FOREIGN PATENT DOCUMENTS

| CN | 1106744 A | 8/1995 |
| CN | 2347608 Y | 11/1999 |

(Continued)

OTHER PUBLICATIONS

Hanafy el al., "Ancient Egyptian Medicine", Urology, vol. IV, No. 1, 1974, pp. 114-120.

(Continued)

*Primary Examiner* — Ariana Zimbouski
*Assistant Examiner* — Stephanie Kim
(74) *Attorney, Agent, or Firm* — Coloplast Corp., Coloplast A/S; Nick Baumann (57) ABSTRACT

A urinary collecting bag comprising a bag part configured for being collapsed in a storage configuration and for being unfolded in a use configuration. A first attachment part and a second attachment part comprise cooperating coupling means which couple first and second attachment parts together in the collapsed storage configuration of the bag part. In the unfolded use configuration of the bag part; the first and second attachment parts are disconnected at said coupling means. A urinary catheter assembly comprising the urinary collecting bag and a urinary catheter is also provided.

15 Claims, 6 Drawing Sheets

(56) References Cited

U.S. PATENT DOCUMENTS

| | | |
|---|---|---|
| 3,321,097 A | 5/1967 | Solowey |
| 3,421,509 A | 1/1969 | Fiore |
| 3,444,860 A | 5/1969 | Harrell |
| 3,648,704 A | 3/1972 | Jackson |
| 3,683,928 A | 8/1972 | Kuntz |
| 3,750,875 A | 8/1973 | Juster |
| 3,762,399 A | 10/1973 | Riedell |
| 3,794,042 A | 2/1974 | De Klotz |
| 3,854,483 A | 12/1974 | Powers |
| 3,894,540 A | 7/1975 | Bonner |
| 3,930,580 A | 1/1976 | Bazell et al. |
| 3,934,721 A | 1/1976 | Juster et al. |
| 3,967,728 A | 7/1976 | Gordon et al. |
| 4,026,296 A | 5/1977 | Stoy et al. |
| 4,062,363 A | 12/1977 | Bonner |
| 4,140,127 A | 2/1979 | Cianci et al. |
| 4,168,699 A | 9/1979 | Hauser |
| 4,170,996 A * | 10/1979 | Wu ............ A61M 25/002 |
| 4,652,259 A | 3/1987 | O'Neil |
| 4,692,154 A | 9/1987 | Singery et al. |
| 4,875,719 A | 10/1989 | Mylett |
| 5,226,530 A | 7/1993 | Golden |
| 5,454,798 A | 10/1995 | Kubalak et al. |
| 5,645,048 A * | 7/1997 | Brodsky et al. .. A61M 16/0463 |
| 5,688,459 A | 11/1997 | Mao et al. |
| 5,895,374 A | 4/1999 | Rodsten |
| 6,045,542 A | 4/2000 | Cawood |
| 6,059,107 A | 5/2000 | Nosted et al. |
| 6,065,597 A | 5/2000 | Pettersson et al. |
| 6,073,759 A | 6/2000 | Lamborne et al. |
| 6,090,075 A | 7/2000 | House |
| 6,117,120 A | 9/2000 | Heininger |
| 6,391,010 B1 | 5/2002 | Wilcox |
| 6,402,726 B1 | 6/2002 | Genese |
| 6,544,240 B1 | 4/2003 | Borodulin et al. |
| 6,578,709 B1 | 6/2003 | Kavanagh et al. |
| 6,602,244 B2 | 8/2003 | Kavanagh et al. |
| 6,634,498 B2 | 10/2003 | Kayerod et al. |
| 6,899,355 B2 | 5/2005 | Klein et al. |
| 6,986,868 B2 | 1/2006 | Madsen |
| 7,311,698 B2 | 12/2007 | Tanghoj et al. |
| 7,380,658 B2 | 6/2008 | Murray et al. |
| 7,886,907 B2 | 2/2011 | Murray et al. |
| 8,011,505 B2 | 9/2011 | Murray et al. |
| 8,205,745 B2 | 6/2012 | Murray et al. |
| 8,523,843 B2 | 9/2013 | Kavanagh et al. |
| 8,720,685 B2 | 5/2014 | Murray et al. |
| 8,740,863 B2 | 6/2014 | Nestenborg et al. |
| 9,028,858 B2 | 5/2015 | Nielsen et al. |
| 9,072,862 B2 | 7/2015 | Murray et al. |
| RE47,513 E | 7/2019 | Murray et al. |
| 10,758,704 B2 | 9/2020 | Hickmott et al. |
| 2001/0001443 A1 | 5/2001 | Kayerod et al. |
| 2002/0144920 A1 | 10/2002 | Samuels |
| 2002/0151834 A1 | 10/2002 | Utterberg |
| 2002/0193762 A1 | 12/2002 | Suydam |
| 2003/0060807 A1 | 3/2003 | Tanghoj et al. |
| 2005/0015076 A1 | 1/2005 | Giebmeyer et al. |
| 2005/0061698 A1 | 3/2005 | Delaney et al. |
| 2005/0070882 A1 | 3/2005 | McBride |
| 2005/0107860 A1 | 5/2005 | Ignagni et al. |
| 2005/0261664 A1 | 11/2005 | Rome et al. |
| 2006/0025753 A1 | 2/2006 | Kubalak et al. |
| 2006/0111681 A1 | 5/2006 | Vernon |
| 2006/0142737 A1 | 6/2006 | Tanghoj |
| 2006/0161115 A1 | 7/2006 | Fangrow |
| 2006/0196783 A1 | 9/2006 | Bruun et al. |
| 2007/0225687 A1 | 9/2007 | House |
| 2008/0171992 A1 | 7/2008 | House |
| 2008/0172016 A1 | 7/2008 | House |
| 2009/0208368 A1 | 8/2009 | Waldrep et al. |
| 2011/0114520 A1 | 5/2011 | Matthison-Hansen |
| 2011/0120892 A1 | 5/2011 | Frederiksen et al. |
| 2011/0160662 A1 | 6/2011 | Stout et al. |
| 2011/0160704 A1 | 6/2011 | Park |
| 2011/0172491 A1 | 7/2011 | Piskun et al. |
| 2011/0230864 A1 | 9/2011 | House |
| 2011/0251572 A1 * | 10/2011 | Nishtala et al. .......... A61F 5/44 |
| 2011/0295239 A1 | 12/2011 | Gustavsson |
| 2012/0165790 A1 | 6/2012 | Gustavsson et al. |
| 2012/0271282 A1 | 10/2012 | Schertiger et al. |
| 2012/0316515 A1 | 12/2012 | Terry |
| 2013/0161208 A1 | 6/2013 | Gustavsson |
| 2013/0165867 A1 | 6/2013 | Isaacson et al. |
| 2013/0186778 A1 | 7/2013 | Terry |
| 2013/0261607 A1 | 10/2013 | Nielsen |
| 2013/0261608 A1 | 10/2013 | Tanghøj |
| 2013/0292286 A1 | 11/2013 | Van Groningen et al. |
| 2013/0327664 A1 | 12/2013 | Tanghøj |
| 2013/0338615 A1 | 12/2013 | Zeller |
| 2014/0194842 A1 * | 7/2014 | Schertiger et al. ..... A61M 1/64 |
| 2014/0262859 A1 | 9/2014 | Knapp et al. |
| 2015/0068927 A1 | 3/2015 | Mcburney et al. |
| 2015/0112314 A1 | 4/2015 | Gustavsson et al. |
| 2015/0133898 A1 | 5/2015 | Murray et al. |
| 2015/0173937 A1 | 6/2015 | Jackson |
| 2015/0202421 A1 | 7/2015 | Ma et al. |
| 2015/0250656 A1 | 9/2015 | Maksimow |
| 2015/0258305 A1 | 9/2015 | Dye |
| 2015/0265801 A1 | 9/2015 | Rostami |
| 2015/0306342 A1 | 10/2015 | Rostami et al. |
| 2016/0015929 A1 | 1/2016 | Tanghoej et al. |
| 2016/0038713 A1 | 2/2016 | Kearns et al. |
| 2016/0038717 A1 | 2/2016 | Murray et al. |
| 2016/0193447 A1 | 7/2016 | Matthiassen |
| 2017/0000978 A1 | 1/2017 | Murray et al. |
| 2017/0203910 A1 | 7/2017 | Buse et al. |
| 2017/0216557 A1 | 8/2017 | Kearns et al. |
| 2018/0169377 A1 * | 6/2018 | Hickmott et al. . A61M 25/0111 |
| 2020/0222659 A1 | 7/2020 | Schertiger et al. |
| 2021/0290895 A1 | 9/2021 | Nielsen et al. |

FOREIGN PATENT DOCUMENTS

| | | |
|---|---|---|
| CN | 1718940 A | 1/2006 |
| CN | 1795024 A | 6/2006 |
| CN | 101132826 A | 2/2008 |
| CN | 101803968 A | 8/2010 |
| CN | 202173621 U | 3/2012 |
| CN | 102654224 A | 9/2012 |
| CN | 102892452 A | 1/2013 |
| CN | 103127597 A | 6/2013 |
| CN | 103301551 A | 9/2013 |
| CN | 103791132 A | 5/2014 |
| CN | 103945893 A | 7/2014 |
| CN | 104379210 A | 2/2015 |
| CN | 204840604 U | 12/2015 |
| DE | 2227416 A1 | 12/1972 |
| DE | 2458217 A1 | 6/1976 |
| DE | 10213411 A1 | 10/2003 |
| DE | 10334372 A1 | 2/2005 |
| DE | 102009031447 A1 | 1/2011 |
| EP | 0166998 A2 | 1/1986 |
| EP | 0217771 A1 | 4/1987 |
| EP | 0679506 A1 | 11/1995 |
| EP | 0923398 A1 | 6/1999 |
| EP | 1018323 A1 | 7/2000 |
| EP | 1312385 A1 | 5/2003 |
| EP | 2072075 A1 | 6/2009 |
| EP | 2423125 A1 | 2/2012 |
| EP | 2423126 A1 | 2/2012 |
| EP | 2423127 A1 | 2/2012 |
| EP | 2695636 A1 | 2/2014 |
| EP | 3210909 A1 | 8/2017 |
| EP | 3392167 A1 | 10/2018 |
| GB | 0322426 A | 12/1929 |
| GB | 2007507 A | 5/1979 |
| JP | 55-012265 A | 1/1980 |
| JP | 2001-139059 A | 5/2001 |
| JP | 2007-533331 A | 11/2007 |
| JP | 2009-279456 A | 12/2009 |
| JP | 2014023605 A | 2/2014 |
| RU | 2012129843 A | 1/2014 |
| RU | 2013130998 A | 1/2015 |

(56) References Cited

FOREIGN PATENT DOCUMENTS

| | | |
|---|---|---|
| RU | 2013131785 A | 1/2015 |
| RU | 2584649 C2 | 5/2016 |
| RU | 2598811 C2 | 9/2016 |
| WO | 92/04932 A1 | 4/1992 |
| WO | 94/06377 A1 | 3/1994 |
| WO | 94/16747 A1 | 8/1994 |
| WO | 96/30277 A1 | 10/1996 |
| WO | 97/26937 A1 | 7/1997 |
| WO | 97/47349 A1 | 12/1997 |
| WO | 98/06642 A1 | 2/1998 |
| WO | 98/11932 A1 | 3/1998 |
| WO | 98/19729 A1 | 5/1998 |
| WO | 2000016843 A1 | 3/2000 |
| WO | 00/30575 A1 | 6/2000 |
| WO | 00/30696 A1 | 6/2000 |
| WO | 00/47494 A1 | 8/2000 |
| WO | 01/52763 A1 | 7/2001 |
| WO | 03/02178 A2 | 1/2003 |
| WO | 03/92779 A1 | 11/2003 |
| WO | 2004/050155 A1 | 6/2004 |
| WO | 2005/004964 A1 | 1/2005 |
| WO | 2005/004970 A1 | 1/2005 |
| WO | 2005/014055 A2 | 2/2005 |
| WO | 2007/022223 A2 | 2/2007 |
| WO | 2007/106431 A2 | 9/2007 |
| WO | 2007/146820 A2 | 12/2007 |
| WO | 2008/146836 A1 | 12/2008 |
| WO | 2009152609 A1 | 12/2009 |
| WO | 2010/006570 A2 | 2/2012 |
| WO | 2010/006620 A1 | 1/2010 |
| WO | 2011/000353 A1 | 1/2011 |
| WO | 2011/079129 A1 | 6/2011 |
| WO | 2011/109393 A1 | 9/2011 |
| WO | 2012/016570 A2 | 2/2012 |
| WO | 2012/016571 A2 | 2/2012 |
| WO | 2013029620 A1 | 3/2013 |
| WO | 2013/049733 A2 | 4/2013 |
| WO | 2014/142917 A1 | 9/2014 |
| WO | 2015/142506 A1 | 9/2015 |
| WO | 2015/184365 A1 | 12/2015 |
| WO | 2016/206701 A1 | 12/2016 |
| WO | 2018/059637 A1 | 4/2018 |
| WO | 2020/015804 A1 | 1/2020 |

OTHER PUBLICATIONS

International Search Report and Written Opinion received for PCT Patent Application No. PCT/DK2019/050418, dated Apr. 20, 2020, 9 pages.

Nacey et al., "The evolution and development of the urinary catheter", Aust. N.Z. J. Surg., vol. 63, 1993, pp. 815-819.

Sherman, "Medical Device Packaging Handbook", A Series of Reference Books, 1998, pp. 1-11.

* cited by examiner

URINE COLLECTING BAG

The invention relates to a urinary collecting bag for use in collecting urine during catheterisation. A urinary catheter assembly comprising the urinary collecting bag and a urinary catheter is also provided.

SUMMARY OF THE INVENTION

A urinary collecting bag is provided which comprises a bag part of a flexible sheet material. This bag part is configured for being collapsed in a storage configuration and for being unfolded in a use configuration. The bag part defines a cavity for collecting urine. The urinary collecting bag further comprises a first attachment part and a second attachment part, wherein each of the first and second attachment parts comprising cooperating coupling means which couple first and second attachment parts together in the collapsed storage configuration of the bag part, and wherein the first and second attachment parts are disconnected at said coupling means in the unfolded use configuration of the bag part A urinary catheter assembly comprising the urinary collecting bag and a urinary catheter is also provided, as specified.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

A urinary collecting bag is provided. The collecting bag is to be used during catheterisation to safely and hygienically collect urine and store it until it can be disposed.

The urinary collecting bag comprises a bag part of a flexible sheet material. The flexible sheet material is liquid-impermeable, and suitably comprises one or more layers of a polymeric material such as e.g. polyester, polypropylene, or blends or co-polymers thereof. The bag part defines a cavity for collecting urine.

Embodiments relate to the bag part comprising two sheets of flexible sheet material welded along the edges to define the cavity for collecting urine. Embodiments relate to the bag part comprising a single sheet of flexible sheet material folded over and welded along the edges to define the cavity for collecting urine. Such embodiments provide easy simple envelope-type construction, which allows easy incorporation of additional elements.

The bag part of the urinary collecting bag is configured for being collapsed in a storage configuration and for being unfolded in a use configuration. This dual configuration is enabled by the bag part being a flexible sheet material.

In the collapsed configuration, the bag part may have a maximum dimension of 100 mm, preferably less than 50 mm in the largest extension. In this manner, it is small enough to be contained and transported in a user's bag or pocket.

The urinary collecting bag further comprises a first attachment part and a second attachment part. First and second attachment parts are typically made of rigid polymer, e.g. a thermoplastic polymer such as polyester, polypropylene, or blends or co-polymers thereof. They have a regular three-dimensional shape with a general elongate form about a central axis. Generally, first and second attachment parts have a plane of symmetry passing through the central axis. Typically, at least a part of each first and second attachment parts has an overall cylindrical shape.

Figure 2:
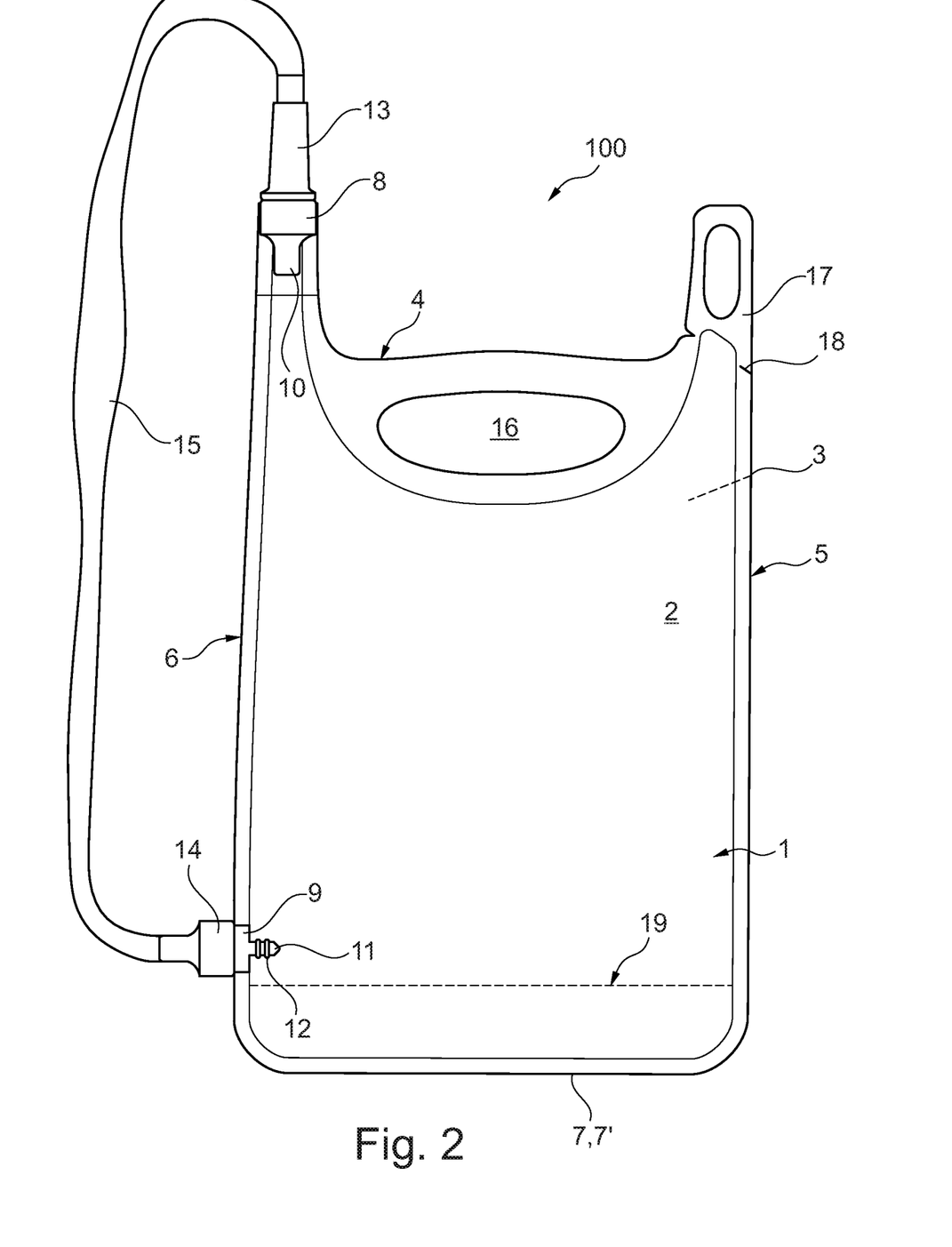
FIG. 2 illustrates a urinary catheter assembly with collecting bag and urinary catheter in the unfolded use configuration.
Figure 3:
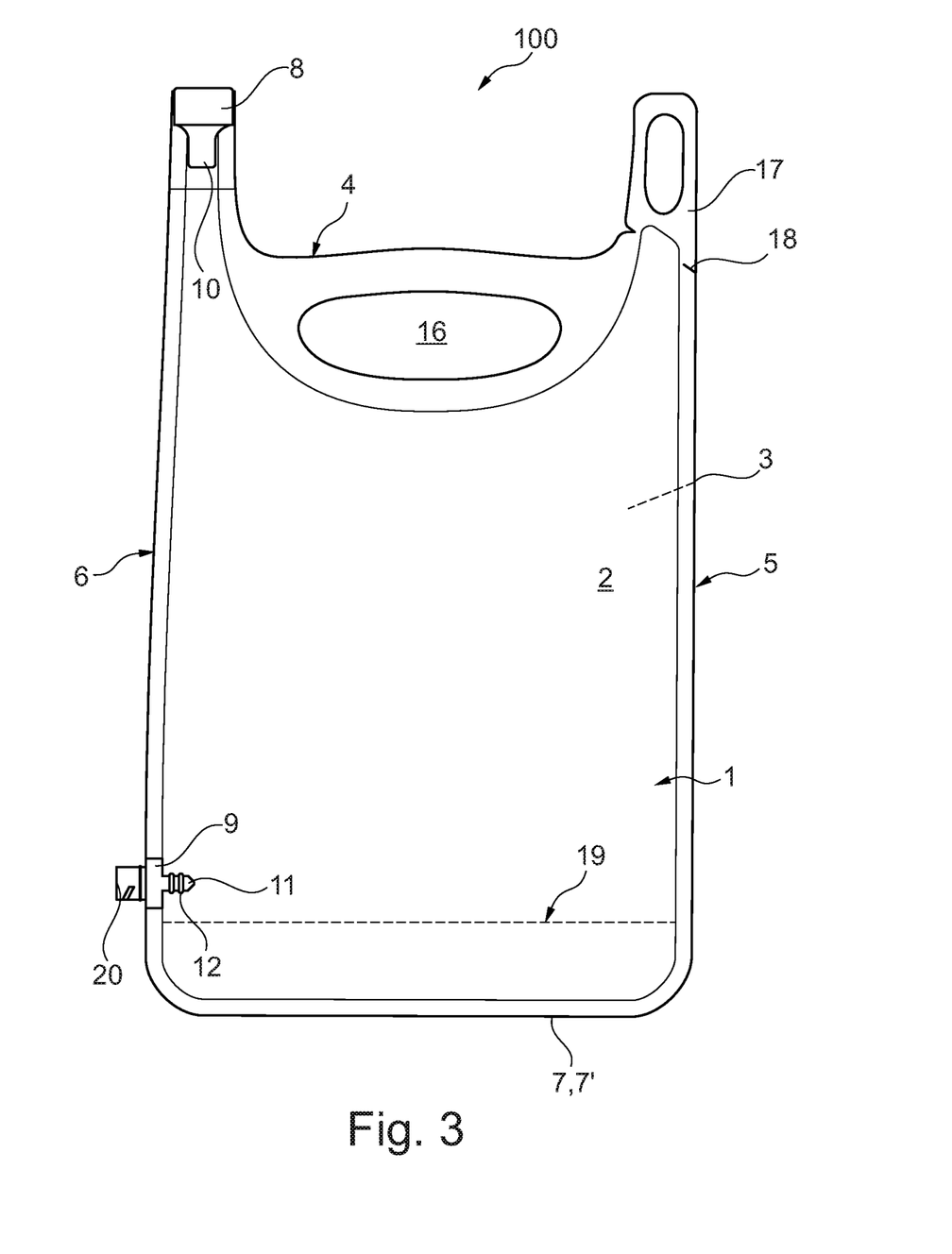
FIG. 3 illustrates urinary collecting bag in unfolded use configuration
Figure 4:
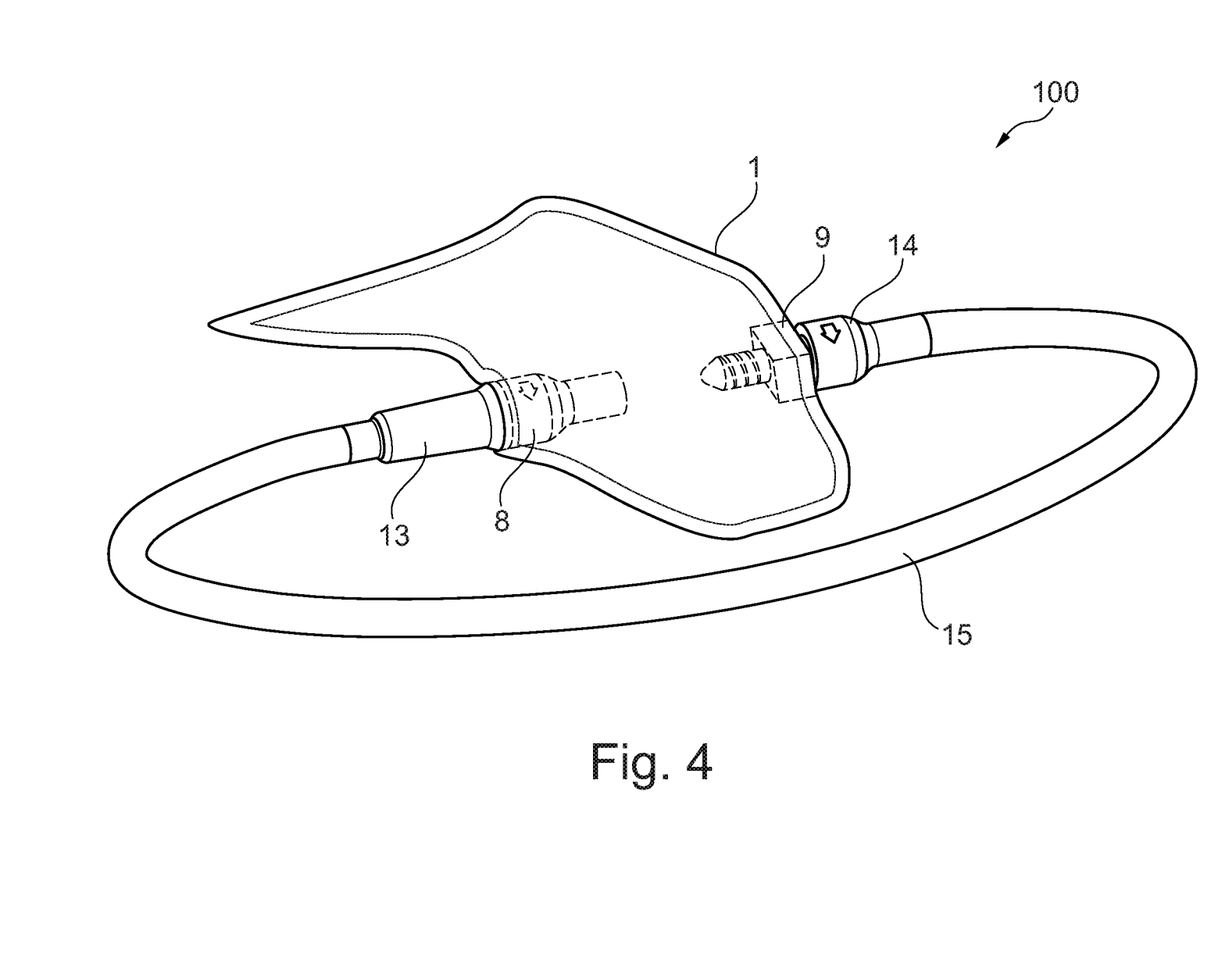
FIG. 4 illustrates a perspective view of a urinary catheter assembly with collecting bag and urinary catheter in the unfolded use configuration.

In one embodiment, at least the first attachment part—and optionally the second attachment part—comprise a fluid conduit, allowing passage of fluid (e.g. urine) between the exterior of the bag part and the urine cavity. In FIGS. 2-4, the second attachment part is shown as not comprising a fluid conduit.

For ease of manufacture, the first and the second attachment parts may each be individually located in a welded edge of the bag part. The first and the second attachment parts may be in the same welded edge (e.g. a top edge), or in separate welded edges. This arrangement avoids the creation of additional openings in the bag part for the attachment parts.

Each of the first and second attachment parts comprises cooperating coupling means, which couple first and second attachment parts together in the collapsed (storage) configuration of the bag part, and wherein the first and second attachment parts are disconnected at said coupling means in the unfolded (use) configuration of the bag part.

In other words, by engaging the cooperating coupling means on first and second attachment parts with each other, the bag part can be maintained in the collapsed storage configuration. By disconnecting the cooperating coupling means on the first and the second attachment parts from each other, the bag part can be unfolded into the use configuration.

In the unfolded use configuration, the bag part may have a liquid capacity of at least 250 mL, such as at least 500 mL, at least 1 L or at least 2 L. For example, a 1 L capacity can be provided by an "envelope-type" construction having dimensions of approximately 171 mm×289 mm. In this manner, it is large enough to receive and temporarily store urine from a user.

By means of the urinary collecting bag having the above features, a compact storage configuration is achieved in a simple manner, using components (e.g. first and second attachment parts) which allow easy connection or integration of a urinary catheter. Portability is thus provided, which is useful in situations where bathroom facilities (e.g. a toilet) are not readily available. Additionally, in this arrangement of features, the bag part of the collecting bag provides protection for the catheter, or parts thereof.

The coupling means comprises two parts which engage and release mechanically. One part of the coupling means is comprised in the first attachment part, and the other part of the coupling means is comprised in the second attachment part.

The first attachment part may comprise a male coupling part of said coupling means, and the second attachment part comprises a female coupling part of said coupling means. The reverse configuration is also possible.

Figure 6A:
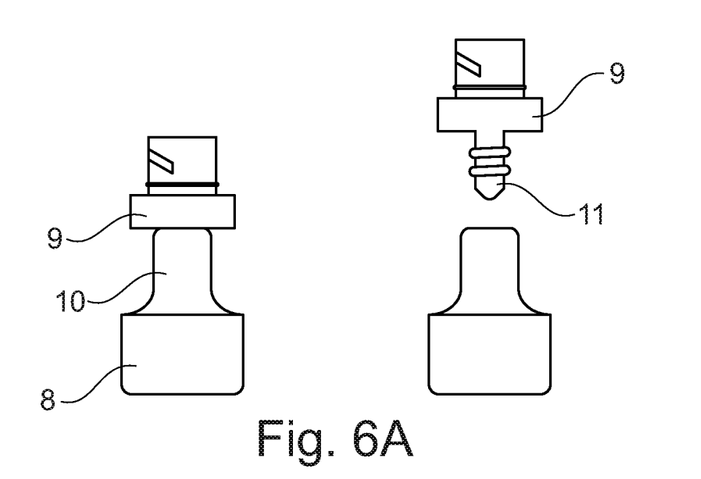
FIGS. 6A-6C illustrate various embodiments of the coupling means.
Figure 6B:
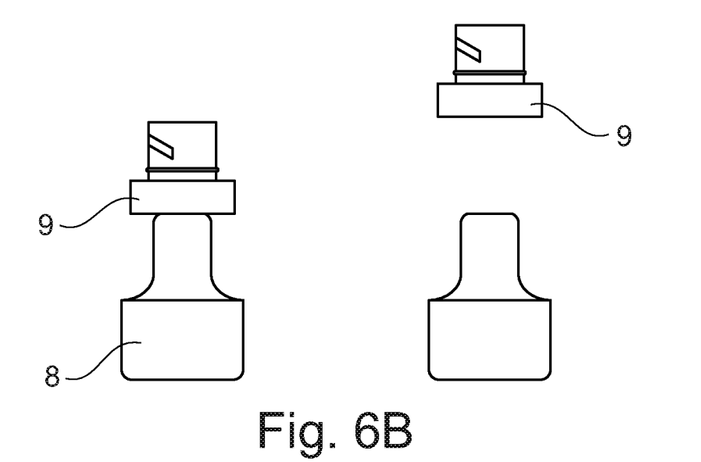
Figure 6C:
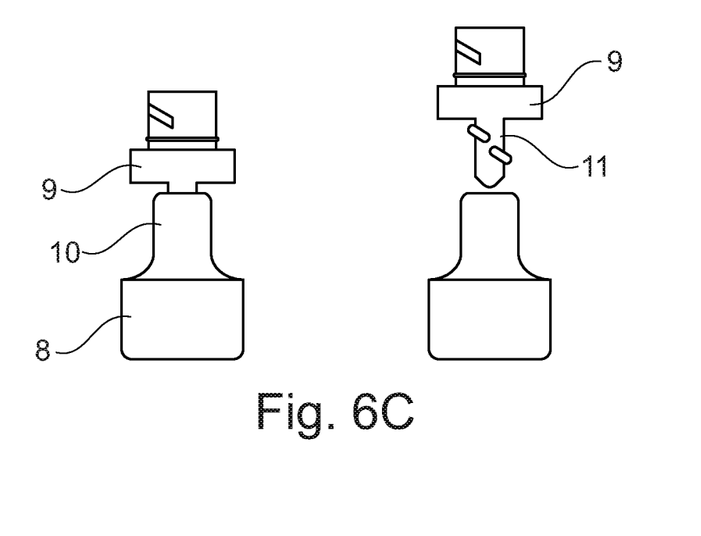

The particular coupling means may be selected according to the requirements of the urinary collecting bag and/or the user. In one embodiment, the coupling means is selected from a friction coupling, a bayonet coupling, a break-off coupling or a threaded coupling. Various coupling means are illustrated in FIGS. 6A-6C.

A friction coupling requires that at least a part of one of the first and second attachment parts is designed to penetrate or otherwise interlock with at least a part of the other attachment part and be held in place through friction. One or more seals may be included in the coupling between first and second attachment parts, to obtain the desired level of friction. An example of a friction coupling is a simple plug in one attachment means, which engages with a socket in the other attachment means.

A break-off coupling requires that at least a part of the first attachment part is attached to at least a part of the second attachment part. Attachment takes place either via adhesive between first and second attachment parts or a weakened joint between co-moulded first and second attachment parts. Application of force breaks the coupling and the first and second attachment parts can be disconnected. Although this variant is simple to construct, it does not allow for re-coupling of first and second attachment parts once broken off.

The person skilled in the art will be able to design a suitable bayonet coupling or threaded coupling as required. The thread of a threaded coupling may be short, so that a user only has to turn the coupling about 90 degrees or even less, such as 60 degrees, to disconnect the coupling. The threaded coupling has the advantage that it is easy to use even for users having poor hand dexterity.

Suitably, the coupling means is re-closable. Re-closable coupling means allows for a hygienic handling of the urinary collecting bag throughout the entire procedure from removing it from the storage package to disposal of the product.

Embodiments relate to the first and second attachment means being arranged to couple the first and second attachment parts together in the storage position via the cavity of the bag part. By coupling via the cavity of the bag part in this manner, a small package can be obtained.

Furthermore—in the storage configuration—the first and the second attachment parts may be coupled together by means of the coupling means via the cavity of the bag part; and the bag part may be wrapped and/or folded about the coupled first and second attachment parts. In this manner, a compact storage configuration for the urinary collecting bag is defined.

It may be useful to determine the relative placement of the first and second attachment parts, so that liquid flow is directed and contained in the best manner. Embodiments therefore relate to—in the unfolded use configuration—the bag part comprising a lower edge and at least one wall of flexible sheet material extending in an upwards direction from said lower edge. The bag part has a lower portion and an upper portion, in which the upper portion is arranged above the lower portion in said upwards direction, wherein at least one of the first and the second attachment parts is located in the upper portion of the bag part. Suitably, the first attachment part is located in the upper portion of the bag part, while the second attachment part is located in the lower portion of the bag part. As an alternative, the first attachment part is located in the upper portion of the bag part and the second attachment part is located in the upper portion of the bag part.

The "lower portion" is defined as being the portion of the bag part between the lower edge and a median line dividing the bag part in two equal halves in the "upwards direction". The "upper portion" is the remainder of the bag part between this median line and the upper edge of the bag part.

Figure 5A:
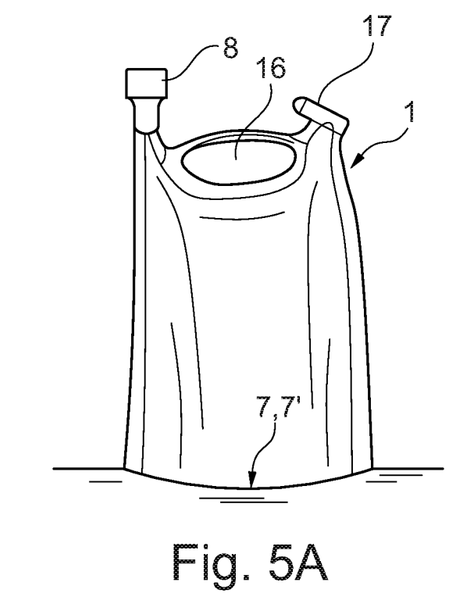
FIG. 5A illustrates a free-standing urinary collecting bag in the unfolded use configuration.

The urinary collecting bag may be designed to be free-standing; i.e. it can support its own weight and the weight of introduced urine when placed on a horizontal surface. This is best illustrated in FIG. 5A. In this embodiment, therefore, the lower edge forms a base upon which the urinary collecting bag can stand freely when placed on a horizontal surface. The base at the lower edge can be formed by additional materials and/or appropriate folds in the bag part. In one embodiment, therefore, the bag part comprises additional support element in the lower portion thereof; which—together with the flexible sheet material of the bag part—forms the base of the bag part. The additional support element is formed of flexible sheet material, such that lower edge of the bag part can be expanded. This construction can be easily integrated into the bag part, via e.g. the welding techniques set out above, and is best illustrated in FIG. 5C.

Embodiments relate to the urinary collecting bag comprising one or more bag handles and/or one or more hanging means arranged in the upper portion thereof when the bag part is in the unfolded use configuration. Hanging means can take the form of a loop, or alternatively a hook element. Bag handles and hanging means allow the urinary collecting bag to be easily carried and to be hung on a hook or support if required. For ease of construction, the bag handles or hanging devices typically take the form of cut-outs in the flexible sheet material of the bag part, as shown in FIGS. 2, 3 and 5A. Alternatively, the bag handles or hanging means comprise separate elements which are joined to the bag during manufacture.

Embodiments relate to the urinary collecting bag comprising one or more sealed openings arranged in the upper portion thereof when the bag portion is in the unfolded use configuration. By opening the sealed opening, the bag can be emptied after use.

Figure 5B:
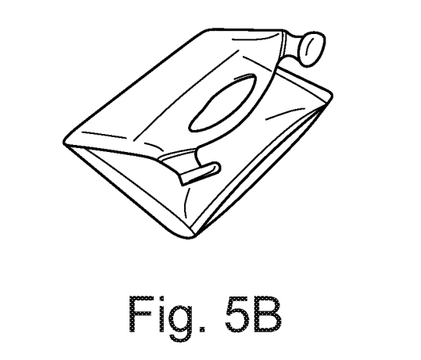
FIG. 5B illustrates how the urinary collecting bag can be folded.
Figure 5C:
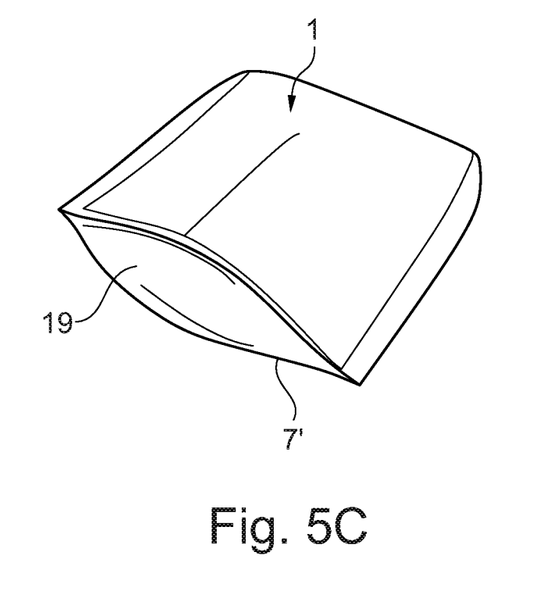
FIG. 5C is a three-dimensional view showing the base of a urinary collecting bag.
Figure 5D:
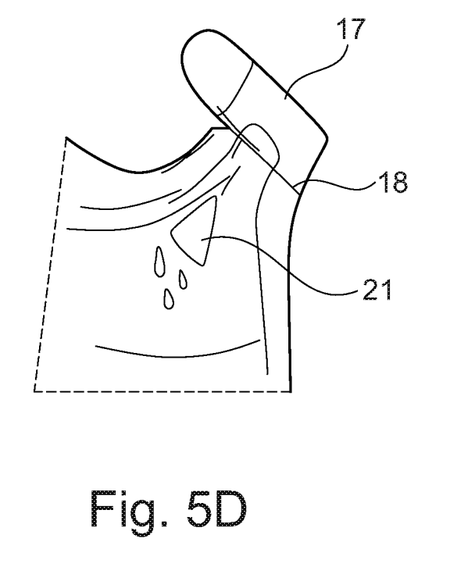
FIG. 5D illustrates a tear-off section which can be removed to empty the urinary collecting bag.

In the embodiment illustrated in FIG. 5D, the sealed opening takes the form of a tear-off part, which can be separated from the remainder of the bag part by a user gripping and tearing-off said tear-off part. Such a tear-off part can be formed by a weakening in the flexible sheet material of the bag part. Alternatively, the sealed opening can take the form of a channel which is stoppered with a plug or similar. When a user removes the plug, the bag can be emptied. In the embodiment where the second attachment part does not comprise a fluid conduit, the second attachment may be a plug in a sealed opening, which can be used to empty the bag after use.

A urinary catheter assembly comprising a urinary collecting bag as defined herein and further comprising a urinary catheter is also provided.

Urinary catheter assemblies for draining the bladder are used for intermittent as well as indwelling or permanent catheterisation. Typically, urinary catheters are used by patients suffering from urinary incontinence or by disabled individuals like paraplegics or tetraplegics, who may have no control permitting voluntary urination and for whom catheterisation may be the way of urinating.

Urinary catheters are divided into two major groups of catheters, indwelling catheters and intermittent catheters. Indwelling catheters are typically inserted into the urethra and the bladder by medical personal (i.e. a trained professional, typically a nurse or physician) and has means for retaining the catheter inside the bladder for up to two weeks or more. Indwelling catheters are soft and flexible since they have to remain in the urethra for weeks. Indwelling catheters empty the bladder continuously.

Intermittent catheters are typically inserted by the user him- or herself and sits only in the urethra and bladder for as long as it takes to empty the bladder—e.g. for about 5-10 minutes. Intermittent catheters are used every 4-6 hours to empty the bladder corresponding roughly to the interval with which people having no urinary problems will usually go to the bathroom. Intermittent catheters are typically more rigid than indwelling catheters since they have to be inserted by the user him-/herself and since they do not need to sit in the urethra for days or weeks. An important feature for the intermittent catheter is to ease the insertion into the urethra. This is done by providing the intermittent catheter with a low frictious surface. A low friction surface may be obtained by providing the intermittent urinary catheters with a hydrophilic coating that needs to be wetted prior to use and thereby absorbs a considerable amount of liquid. Such a hydrophilic coating will provide a very lubricious surface that has very low-friction when the catheter is to be inserted. Hydrophilic coated catheters, where the coating absorbs a considerable amount of liquid for a low frictious surface (swelling degree >100%), will not be suitable for indwelling catheters, because the hydrophilic surface coating would stick inside the mucosa of the urethra if left inside the body for a longer period of time, due to the hydrophilic coating transforming from being highly lubricious when fully wetted to being adhesive when the hydration level of the coating is reduced.

The urinary catheter as described herein is configured to be used intermittently. The urinary catheter described herein has a hydrophilic surface in the form of a hydrophilic coating. The hydrophilic coating may be provided only on the insertable part of the catheter. The hydrophilic surface coating is of the kind which, when hydrated or swelled using a swelling medium, reduces the friction on the surface area of the catheter which is intended to be inserted into the urinary channel of a user corresponding to the insertable part of the catheter.

An intermittent hydrophilic catheter differs from an indwelling catheter in that the hydrophilic surface coating of such a catheter is not suitable for indwelling use, because the surface coating tends to stick inside the mucosa of the urethra if left inside the body for a period exceeding 5-20 minutes, due to the hydrophilic coating transforming from being highly lubricious when fully wetted (95% weight water) to being adhesive when the hydration level of the coating is reduced (<75% weight water).

In the storage condition, the urinary catheter assembly comprises a medium for activating the hydrophilic surface coating of the catheter. The activating medium may be a water based substance, such as sterile water, or a saline-solution. Furthermore, the activating medium may be in the form of a vapour contributing material, such as a wetted sponge, woven or non-woven material comprising a vapour contributing liquid. By introducing a vapour contributing material into the package, the vapour will over time hydrate the hydrophilic coating ensuring that the coating is activated and that the hydrophilic coating provides a low-friction surface for the catheter.

In an embodiment, the catheter is a male catheter meaning that the catheter has an insertion length of at least 250 mm, more preferred at least 300 mm.

The urinary catheter is provided with an insertion tip at a proximal end of the urinary catheter and an outlet at a distal end of the urinary catheter In this text, whenever referring to a proximal end of an element of the urine collecting bag or the urinary catheter assembly, the referral is to the end adapted for insertion. Whenever referring to the distal end of an element, the referral is to the end opposite the insertion end. In other words, the proximal end is the end closest to the user, when the catheter is to be inserted and the distal end is the opposite end—the end furthest away from the user when the catheter is to be inserted.

The longitudinal direction is the direction along the catheter from the distal to the proximal end. The transverse direction is the direction perpendicular to the longitudinal direction, which corresponds to the direction across the shaft of the catheter.

The urinary catheter comprises a main tubular portion extending from the distal end to the proximal end. A tip portion is positioned at a proximal portion of the main tubular portion. An eyelet portion with eyelets is positioned distally of the tip portion. The tip portion may comprise a proximal rounded closed end of the tubular portion thereby defining the insertion tip. The eyelets may serve the purpose of allowing urine into the inner lumen of the tubular portion. The tip portion may be a Nelaton tip, where the proximal end is simply closed off providing a half-spherical closed end. The tip portion may also be a so-called flex-tip, where a distal portion of the tip portion has an outer circumference, which is less than the circumference of the main tubular part. This distal portion of the tip portion is proximally followed by a bulb-shaped or olive-shaped insertion tip. The tip portion may be integrally moulded with the main tubular part—either as 1 component or 2 component moulding—or it may be provided as a separate element and then attached to the main tubular portion, e.g. by welding or adhering. The tip portion and eyelet portion may also be made by modifying the main tubular part, i.e. by punching the eyelets and rounding the proximal end to close it off.

The urinary catheter may be made of a polyurethane material (PU) or polyvinyl chloride (PVC) or poly-olefins such as a polyethylene (PE).

Usually urinary catheters for intermittent use are from size 8 FR to size 18 FR. FR (or French size or Charriere (Ch)) is a standard gauge for catheters approximately corresponding to the outer circumference in mm. More accurately, the outer diameter of the catheter in mm corresponds to FR divided by 3. Thus, 8 FR corresponds to a catheter with an outer diameter of 2.7 mm and 18 FR corresponds to a catheter with an outer diameter of 6 mm.

A handle is slidingly disposed on the urinary catheter. The handle is suitably an element of moulded plastic, having a channel through or along which the urinary catheter can slide. The handle is used to hold and guide the catheter into the urinary tract, while maintaining the catheter in a sterile condition. The handle is releasably attached to the second attachment part of the urinary collecting bag; via a releasable connector which can e.g. be a threaded connector, a bayonet connector, or a friction connector.

A collapsible, flexible sleeve attached is to the handle and is configured to cover the urinary catheter from the outlet to the tip portion in an extended configuration of the urinary catheter assembly. By being configured to cover the urinary catheter from the outlet to the insertion tip is meant that the sleeve covers a majority of the longitudinal extent of the catheter in an extended configuration. In an embodiment, the sleeve is liquid tight and configured to store liquid in the cavity provided by the sleeve, handle and connector. This means that the swelling medium or activating medium needed for the hydrophilic coating can be contained inside the sleeve so that the hydrophilic surface on the catheter is activated by the liquid. The material for the sleeve may, for example, be a foil-material of polyethylene, such as a soft polyethylene of LDPE. The material may also be an ethylene based plastomer. It is contemplated that materials having a flexural modulus of less than 300 MPa measured according to ISO 178 will be adequately collapsible. By adequately collapsible is meant that the sleeve provides only little resistance to being collapsed towards the distal end. Thus, sleeve materials having a flexural modulus of less than 100 MPa may also be used. The sleeve provides an antimicrobial barrier.

The sleeve is attached to a connector at the outlet, and the connector is attached to the first attachment part of the urinary collecting bag.

Suitably, the connector is releasably attached to the first attachment part of the urinary collecting bag. Preferably, the connector is attached to the first attachment part of the urinary collecting bag in a non-releasable manner (e.g. using adhesive or welding), so that a user does not unintentionally disconnect the catheter from the urinary collecting bag.

The connector may be configured to contain and protect the tip portion of the catheter prior to use. Accordingly, the connector may be made of a rigid material, and have a storage cavity so that the insertion tip can be protected inside the connector prior to use. Thereby, in the storage condition, the urinary catheter assembly may be in the form of a ring-shaped assembly, completely contained inside the cavity provided by the sleeve, handle, bag and connector. A flexible insertion tip portion, meaning a tip portion that is easily bendable, may be prone to permanent deformation during storage, unless it is ensured that the tip portion is prevented from being bent during storage. This is obtained by providing the connector of a relatively rigid material so that the storage cavity provides protection against bending for the tip portion.

In the collapsed storage configuration of the bag part—connector and handle are coupled together via the first and second attachment parts. In the unfolded use configuration of the bag part—first and second attachment parts are disconnected.

To use the catheter, the handle is detached from the second attachment part of the urinary collecting bag. Following unfolding or unrolling of the urinary catheter assembly, the urinary catheter with attached urinary collecting bag is ready to be used. The sleeve further provides the user with the possibility of gripping and holding the urinary catheter so that it is easier to use.

The connector, handle, first and second attachment parts and bag part define a cavity encapsulating an entirety of the urinary catheter in the storage configuration. In a use condition or extended configuration of the assembly, the connector and handle are detached from each other and, typically, any liquid (e.g. activating medium for the catheter) will be drained out from the cavity.

One advantage of the urinary catheter assembly is that the sleeve, bag, connector and handle provide a complete enclosure (a cavity) for the urinary catheter, so that in the storage condition, the sterility is not compromised in any way—even as the catheter assembly is removed from an optional storage package.

DETAILED DESCRIPTION OF THE DRAWING

Figure 1:
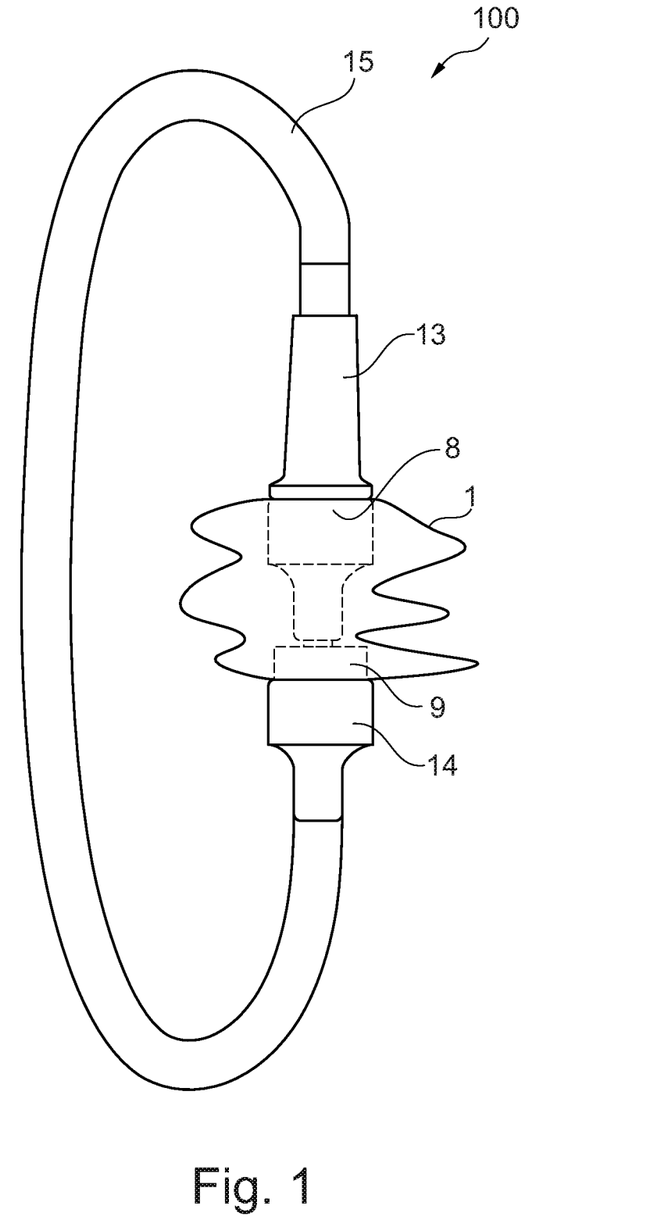
FIG. 1 illustrates a urinary catheter assembly with collecting bag and urinary catheter in the collapsed storage configuration.

FIG. 1 illustrates a urinary catheter assembly 100 as described herein in the collapsed storage configuration comprising urinary collecting bag 1. FIG. 1 shows first attachment part 8 and second attachment part 9. Connector 13 is attached to the first attachment part 8, preferably in a non-releasable manner. Handle 14 is releasably attached to the second attachment part 9. Sleeve 15 extends between connector 13 and handle 14. A urinary catheter (not shown) is located within sleeve 15, and also extends between connector 13 and handle 14, outside the bag 1.

FIG. 2 illustrates a urinary catheter assembly 100 as described herein in the unfolded use configuration. The collecting bag 1 comprises a first and second sheet 2, 3 of plastic material welded together along the edges, 4, 5, 6, 7. At one edge 4, a first attachment part 8 is welded to the collecting bag 1 by interposing it between the first and second sheet 2, 3, and subsequently welding the sheets to the first attachment part and along the edge 4. At another edge 6, a second attachment part 9 is welded to the collecting bag 1 in a similar manner.

The first attachment part 8 comprises a female coupling part 10 facing inwards into the bag and the second attachment part 9 comprises a male coupling part 11 facing inwards into the bag. The female coupling part 10 and the male coupling part 11 are configured to be connected to each other as "coupling means" and consist in the illustrated embodiment of a friction fit coupling. In the illustrated embodiment, the male coupling part 11 has a number of protruding ribs 12 allowing for a secure friction fit in the female coupling part 10.

Connector 13 is attached to the first attachment part 8, preferably in a non-releasable manner. Handle 14 is releasably attached to the second attachment part 9. Sleeve 15 extends between connector 13 and handle 14. A urinary catheter (not shown) is located within sleeve 15, and also extends between connector 13 and handle 14.

Bag handle 16 is located along edge 4, while tear-off part 17 is defined by weakening 18 in the bag material.

At the lower edge 7, an additional piece of flexible sheet material 19 is used to form the base 7' of the collecting bag 1.

FIG. 3 illustrates the urinary collecting bag as per FIG. 2 (without the catheter, handle, sleeve and connector) in unfolded use configuration. The elements in this figure correspond to those of FIG. 2.

In particular, this figure illustrates the releasable connector 20 of the second attachment part 9 of the urinary collecting bag 1 which is used to connect the handle 14. In this figure, releasable connector 20 is a threaded connector.

FIG. 4 illustrates the urinary catheter assembly of FIG. 1 in unfolded use configuration, prior to use. The first and second attachment parts 8, 9 are disconnected from each other.

FIGS. 5A-5D illustrate features of a urinary collecting bag 1.

FIG. 5A illustrates bag handle 16 and tear-off part 17. Lower edge 7 is in the form of a base 7', which allows the urinary collecting bag 1 to stand freely on a horizontal surface.

FIG. 5B is an illustration of the urinary collecting bag 1 of FIG. 5A, showing how it can easily fold.

FIG. 5C is an illustration of the urinary collecting bag 1 of FIGS. 5A and 5B, showing flexible sheet material 19 used to form the base 7' of the collecting bag 1.

FIG. 5D is an illustration of the urinary collecting bag 1 of FIG. 5A-5C, showing tear-off part 17 defined by weakening 18 in the bag material. Printed indications 21 indicate a direction of fluid flow to a user.

FIGS. 6A-6C illustrate various embodiments of the coupling means.

In FIG. 6A, first attachment part 8 comprises a female coupling part 10 and second attachment part 9 comprises a male coupling part 11. The illustrated coupling means is a "plug" coupling means, which relies upon friction between male and female coupling parts to provide a releasable coupling.

In FIG. 6B, first attachment part 8 and second attachment part 9 are moulded together and can be broken apart by hand. The illustrated coupling means is therefore a "break-off" coupling means, which relies upon rupture between male and female coupling parts to provide a releasable coupling.

In FIG. 6C, first attachment part 8 comprises a female coupling part 10 and second attachment part 9 comprises a male coupling part 11. The illustrated coupling means is a threaded coupling means, which requires that male coupling part 11 and female coupling part 10 engage via complementary threads.

Embodiments, and features of the various exemplary embodiments described in this application, may be combined with each other ("mixed and matched"), unless specifically noted otherwise.

The invention claimed is:

1. A urinary collecting bag comprising:
   a bag part of a sheet material, said bag part configured to collapse to a collapsed storage configuration and configured to be unfolded into an unfolded use configuration, the bag part defining a cavity for collecting urine, the urinary collecting bag further comprising:
   a first attachment part and a second attachment part, wherein each of the first and second attachment parts comprises cooperating coupling means adapted to couple the first attachment part and the second attachment part together in the collapsed storage configuration; and
   wherein the first attachment part and the second attachment part are disconnected at said cooperating coupling means in the unfolded use configuration;
   wherein at least the first attachment part comprises a fluid conduit between an exterior of the bag part and the urine cavity;
   wherein, when the bag part is in the collapsed storage configuration and the first attachment part and the second attachment part are coupled together, a coupling part of each of the first attachment part and the second attachment part is connected inside the cavity of the bag part.

2. The urinary collecting bag of claim 1, wherein the cooperating coupling means is selected from the group consisting of a friction coupling, a bayonet coupling, a break-off coupling, and a threaded coupling.

3. The urinary collecting bag of claim 1, wherein the second attachment part comprises a fluid conduit between the exterior of the bag part and the urine cavity.

4. The urinary collecting bag of claim 1, wherein, when the bag part is in the unfolded use configuration, the bag part comprises a lower edge and at least one wall of the sheet material extending in an upwards direction from said lower edge; the bag part having a lower portion and an upper portion, in which the upper portion is arranged above the lower portion in said upwards direction, wherein at least one of the first and second attachment parts is located in the upper portion of the bag part.

5. The urinary collecting bag of claim 4, wherein the first attachment part is located in the upper portion of the bag part and the second attachment part is located in the lower portion of the bag part.

6. The urinary collecting bag of claim 4, wherein the first attachment part is located in the upper portion of the bag part and the second attachment part is located in the upper portion of the bag part.

7. The urinary collecting bag of claim 4, wherein the lower edge forms a base upon which the urinary collecting bag is adapted to stand freely when placed on a horizontal surface.

8. The urinary collecting bag of claim 7, wherein the bag part comprises a support element in the lower portion that, in combination with the sheet material of the bag part, forms the base of the bag part.

9. The urinary collecting bag of claim 4, wherein the urinary collecting bag comprises a handle and a hanging means arranged in the upper portion of the bag part.

10. The urinary collecting bag of claim 1, further comprising:
    a sealed opening formed in an upper portion of the bag part, where the sealed opening is adapted to be opened and resealed.

11. The urinary collecting bag of claim 1, wherein the sheet material is a single sheet of liquid-impermeable material folded over on itself and welded along opposing edges to define the cavity for collecting urine.

12. The urinary collecting bag of claim 11, wherein the first attachment part and the second attachment part are each individually sealed within one of the opposing edges of the bag part.

13. A urinary catheter assembly comprising the urinary collecting bag of claim 1, and further comprising:
    a urinary catheter having a hydrophilic surface, the urinary catheter comprising an insertion tip at a proximal end of the urinary catheter and an outlet at a distal end of the urinary catheter,
    a handle slidably disposed on the urinary catheter,
    a sleeve attached to the handle and configured to cover the urinary catheter from the outlet to the insertion tip, with the sleeve attached to a connector at the outlet,
    wherein the connector is attached to the first attachment part of the urinary collecting bag,
    wherein the handle is releasably attached to the second attachment part of the urinary collecting bag,
    wherein, in the collapsed storage configuration of the bag part, the connector and the handle are coupled together, wherein, in the unfolded use configuration of the bag part, the first attachment part and the second attachment part are disconnected.

14. The urinary catheter assembly of claim 13, wherein the connector, the handle, the first attachment part, the second attachment part, and the bag part combine to encapsulate an entirety of the urinary catheter in the collapsed storage configuration.

15. The urinary collecting bag of claim 1, wherein the bag part is wrapped around the first attachment part and the second attachment part when the bag part is in the collapsed storage configuration.

\* \* \* \* \*